(12) United States Patent
Walling et al.

(10) Patent No.: US 7,452,526 B2
(45) Date of Patent: Nov. 18, 2008

(54) DIRECT CONTACT QUENCH CRYSTALLIZATION PROCESS AND COSMETIC PRODUCTS PRODUCED THEREBY

(75) Inventors: David William Walling, Cincinnati, OH (US); Eric Shane Henley, West Harrison, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 582 days.

(21) Appl. No.: 11/069,684

(22) Filed: Mar. 1, 2005

(65) Prior Publication Data

US 2005/0191254 A1   Sep. 1, 2005

Related U.S. Application Data

(60) Provisional application No. 60/549,065, filed on Mar. 1, 2004.

(51) Int. Cl.
*A61Q 15/00*   (2006.01)
*C21D 1/64*   (2006.01)
*A61K 6/00*   (2006.01)
*C21D 1/55*   (2006.01)

(52) U.S. Cl. ....................... 424/65; 424/633
(58) Field of Classification Search .................. 424/65, 424/633
See application file for complete search history.

(56) References Cited

U.S. PATENT DOCUMENTS

| | | | | |
|---|---|---|---|---|
| 4,985,238 A | | 1/1991 | Tanner et al. | |
| 5,603,925 A | * | 2/1997 | Ross et al. | 424/65 |
| 5,891,425 A | * | 4/1999 | Bretzler | 424/65 |
| 5,972,319 A | | 10/1999 | Linn et al. | |
| 6,171,601 B1 | | 1/2001 | Gardlik et al. | |
| 6,187,842 B1 | * | 2/2001 | Kobayashi et al. | 524/58 |
| 6,258,346 B1 | | 7/2001 | Scavone et al. | |
| 6,338,840 B1 | | 1/2002 | Allan et al. | |
| 2003/1132821 | | 6/2003 | Buranachokpaisan | |
| 2004/0086478 A1 | | 6/2004 | Ferrari | |

FOREIGN PATENT DOCUMENTS

WO   WO 02/053109   7/2002

* cited by examiner

*Primary Examiner*—Johann Richter
*Assistant Examiner*—Andriae M Holt
(74) *Attorney, Agent, or Firm*—Vladimir Vitenberg; Andrew J. Hagerty; Brian M. Bolam

(57) ABSTRACT

A process for making a solid cosmetic composition, the process comprising the steps of: forming at least one hot process stream comprising a solvent and a gellant dissolved therein, the hot process stream having a first temperature; forming at least one cold process stream comprising a cosmetic active having a second temperature, wherein the second temperature is at least 5 degrees C. below the first temperature; combining the at least one hot process stream and the at least one cold process stream together in a mixing chamber having no moving parts therein and without applying external source of cooling, to form a substantially homogeneous product stream.

13 Claims, 1 Drawing Sheet

DIRECT CONTACT QUENCH CRYSTALLIZATION PROCESS AND COSMETIC PRODUCTS PRODUCED THEREBY

CROSS REFERENCE TO RELATED APPLICATION

This application claims the benefit under 35 USC 119(e) to U.S. Application No. 60/549,065, filed Mar. 1, 2004.

FIELD OF THE INVENTION

The present invention relates to solid cosmetic products, and more particularly to deodorant and antiperspirant stick compositions and processes for making the same.

BACKGROUND OF THE INVENTION

There are many types of solid deodorant and antiperspirant sticks that are commercially available or otherwise known in the art. These solid sticks are designed to provide effective perspiration and odor control while also being cosmetically acceptable during and after application onto the underarm area of the skin, and are typically packaged in dispensing containers suitable for conventional application of the composition to the skin by a consumer. In this context, "cosmetically acceptable" means that the product glides on smoothly during application, is non-irritating, and results in little or no visible residue (e.g., low residue performance) after application to the skin.

The conventional way of making such solid deodorants and antiperspirants includes combining all ingredients in a heated hold tank. The ingredients are thoroughly mixed and heated to several degrees above the complete melt point of the mixture. Once the ingredients in the heated tank are completely melted and mixed, a small feed stream is pumped through a scraped surface heat exchanger to initiate crystallization. The feed stream then goes through a filler where it is fed into canisters. Some portion of the feed stream can be re-circulated through a second heat exchanger to melt the crystals before being deposited back into the heated hold tank. This process is continued until the hold tank is emptied and a new batch is started. There are several limitations associated with a conventional process described above.

First, the quality of the crystal structure is limited by the process since only a small portion of the process stream is exposed through indirect contact to the cooling media to result in spontaneous nucleation. In a scraped surface heat exchanger the portion of the stream exposed to the chilled surface is increased by the scraping action of the blades to renew and clear the surface for indirect contact. However, the freshly nucleated product that is scraped from the wall is re-introduced into the hot bulk product flow. Near the inlet of the scraped surface heat exchanger the bulk product flow is above the melting point of the just nucleated crystals, so the thermal driving force is for re-melting the just formed crystals. By the exit of the scraped surface heat exchanger the bulk product flow is typically at a temperature below the melting point of the crystalline material, but above it's spontaneous nucleation temperature—this is known in the art as the Metastable Growth Region. In this temperature region, crystalline material can grow on existing crystals, but generally are thermodynamically unable to form new, independent crystals. Accordingly, much of the crystallization occurs in the Metastable Growth Region and results in relatively large, non-uniform crystals that are less than optimal in their ability to harden a solid stick suspension, and resist weeping in soft solid compositions.

Therefore, it would be desirable to create a process that would result in a substantially higher proportion of the stream being crystallized in the spontaneous nucleation region to create a crystal structure with smaller, more uniform crystals that could harden a solid suspension using less total gellant and result in soft solid suspensions that can better resist weeping.

Another disadvantage of the conventional method includes the possibility for heat sensitive ingredients to deteriorate during the period of time required to formulate and completely process a batch at the elevated holding temperatures. Therefore, it would be desirable to create a processing method that would shorten or even eliminate the time period required for the heat sensitive ingredients to be held at elevated temperatures.

Also, the conventional process itself is relatively complex and requires capital equipment with moving parts that can be expensive and require periodic maintenance to keep it in good operating condition. Accordingly, it would be desirable to create a process with no moving parts to reduce capital, maintenance and operating costs.

U.S. Pat. No. 6,338,840 describes a process and an apparatus for forming deodorant or antiperspirant sticks by forming a mobile composition for dispensing into containers or molds under pressure, preferably using a screw extruder, particularly a twin-screw extruder. The process claims the benefit of allowing incorporation of sensitive ingredients and ameliorating sedimentation of particulates. However, this process also appears to have at least some of the same limitations as the above-described conventional process in that only a small portion of the process stream is exposed through indirect contact to the surface of the cooling media. Additionally, the extruder has multiple moving parts that are expensive to maintain.

WO 02/053109 describes a process for preparing a solid free-standing cosmetic composition, whereby the composition is pumped through a cooled pipe without being subjected to mixing during its passage through the pipe. While this process does not employ a forced extrusion, it still requires external cooling means, such as a cooling jacket surrounding the pipe, to nucleate and crystallize the crystal matrix with all the aforementioned limitations.

The present invention comprises a novel and advantageously simple process for making solid cosmetic compositions, such as, for example, deodorant and antiperspirant sticks, while avoiding the limitations of the prior art.

SUMMARY OF THE INVENTION

It has now been discovered that a process for making solid cosmetic compositions, that includes direct contact-quench crystallization by a cooling media provides the benefits of smaller, more uniform crystal size of the resultant composition. Accordingly, the present invention comprises, in one aspect, a process for making a solid cosmetic composition, the process comprising the steps of: forming at least one hot process stream comprising a solvent and a gellant dissolved therein, the hot process stream having a first temperature; forming at least one cold process stream comprising a cosmetic active having a second temperature lower than the first temperature; and combining the at least one hot process stream and the at least one cold process stream together in a mixing chamber having no moving parts therein to form a substantially homogeneous product stream and without applying external source of cooling.

The ratio, by weight, of the hot process stream to the cold process stream at the point of combining the streams together is from about 1:9 to about 3:1. Put another way, the hot process stream may comprise be from about 10 percent to about 75 percent of the cold process stream.

According to the present invention, when the hot and cold process streams are combined together, substantially the entire amount of the hot process stream being combined is virtually instantaneously cooled to a temperature of at least one degree, more specifically at least 5 degrees, and even more specifically at least 10 degrees, C. below the onset of crystallization of a resulting, mixed, product stream.

The second temperature can be at least 5 degrees, more specifically at least 20 degrees, more specifically at least 50 degrees, and even more specifically at least 70 degrees, C. lower than the first temperature.

Beneficially, the step of combining the hot process stream and the cold process stream together may be conducted such as to cause the gellant to cool at a cooling rate of at least 30, and more specifically at least 50, degrees C. per second, thereby crystallizing the gellant and forming the solid cosmetic composition. The process can be continuous or—alternatively—periodic.

The first temperature can be from 1° C. to 50° C. above the onset of crystallization of the hot process stream. The second temperature can be at least 20° C. below the first temperature. In some embodiments, the second temperature can be from 5° C. to 60° C. below the onset of crystallization of the hot process stream.

The solvent can be any material that is liquid at the holding temperature of the hot process stream and that can dissolve or suspend the gellant. The solvent can be selected from the group consisting of cyclic, linear and branched chain silicones. Suitable solvents may comprise, but are not limited to, non-volatile paraffinic hydrocarbon fluids such as those described in U.S. Pat. No. 4,985,238 and anhydrous liquid carriers such as those described in U.S. Pat. No. 6,171,601 or in U.S. Pat. No. 6,258,346 and emollients such as those described in U.S. Pat. No. 5,972,319. Solvent comprising cyclomethicone is believed to be beneficial.

The gellant can be any material which can crystallize from the hot process stream and remain solid at room temperature. Suitable gellants can include, but are not limited to, those described in U.S. Pat. No. 6,258,346 and those described as nucleating agents or gellants in U.S. Pat. No. 6,171,601, or those waxes and wax-like materials described in U.S. Pat. No. 4,985,238 and may be selected from, but not limited to, the group consisting of stearyl alcohol and other fatty alcohols; hydrogenated castor oil; paraffin wax; beeswax; carnauba; candelilla; spermeceti wax; ozokerite; ceresin; baysberry; synthetic waxes, such as Fisher-Tropsch waxes and microcrystalline wax; polyethylenes with molecular weight of about 200 to about 1000 daltons; solid triglycerides; and any mixtures thereof.

The cold process stream comprises a liquid emollient or solvent that is characterized by its ability to disperse an antiperspirant or deodorant active or a cosmetic active. The liquid emollient for the cold process stream may comprise, but is not limited to, the aforementioned solvents for use in the hot process stream. The liquid emollient or solvent can be selected from the group consisting of cyclomethicone, mineral oil; PPG-14 butyl ether; isopropyl myristate; petrolatum; butyl stearate; cetyl octanoate; butyl myristate; myristyl myristate; C12-15 alkylbenzoate (e.g., Finsolv.TM.); octyldodecanol; isostearyl isostearate; octododecyl benzoate; isostearyl lactate; isostearyl palmitate; isobutyl stearate; dimethicone and any mixtures thereof.

If desired, the step of combining the hot process stream and the cold process stream may include combining the hot and cold streams in a pipe having an external source of heating and involving no moving mechanical parts.

In another aspect, the present invention comprises a method of solidifying a cosmetic composition comprising an antiperspirant or deodorant active, the method comprising the steps of: providing a liquid gellant component in a first liquid solvent having a first temperature; providing an active component dispersed in a second liquid solvent having a second temperature lower than the first temperature; combining the liquid gellant component and the active component together so that the active component causes cooling of the gellant component to a temperature of from 35° C. to 55° C., thereby crystallizing the gellant component, wherein cooling of the gellant is conducted by virtue of contacting the gellant with the cold process stream and with no external sources of cooling.

In still another aspect, the present invention comprises a solid cosmetic composition made by the process described herein and comprising an antiperspirant or deodorant active, wherein the average size of gellant crystals in the resulting cosmetic composition is less that about 10 microns.

The process of the present invention is simpler and lower in capital cost relative to the processes of prior art, because it required no external sources of cooling of the combined process stream or moving mechanical (mixing) parts. This process also provides the benefit of processing heat-sensitive components without damaging them because the time during which the hot materials contact cold materials before forming the resulting product's homogeneous structure is minimized by the process.

DETAILED DESCRIPTION OF THE INVENTION

Figure 1:
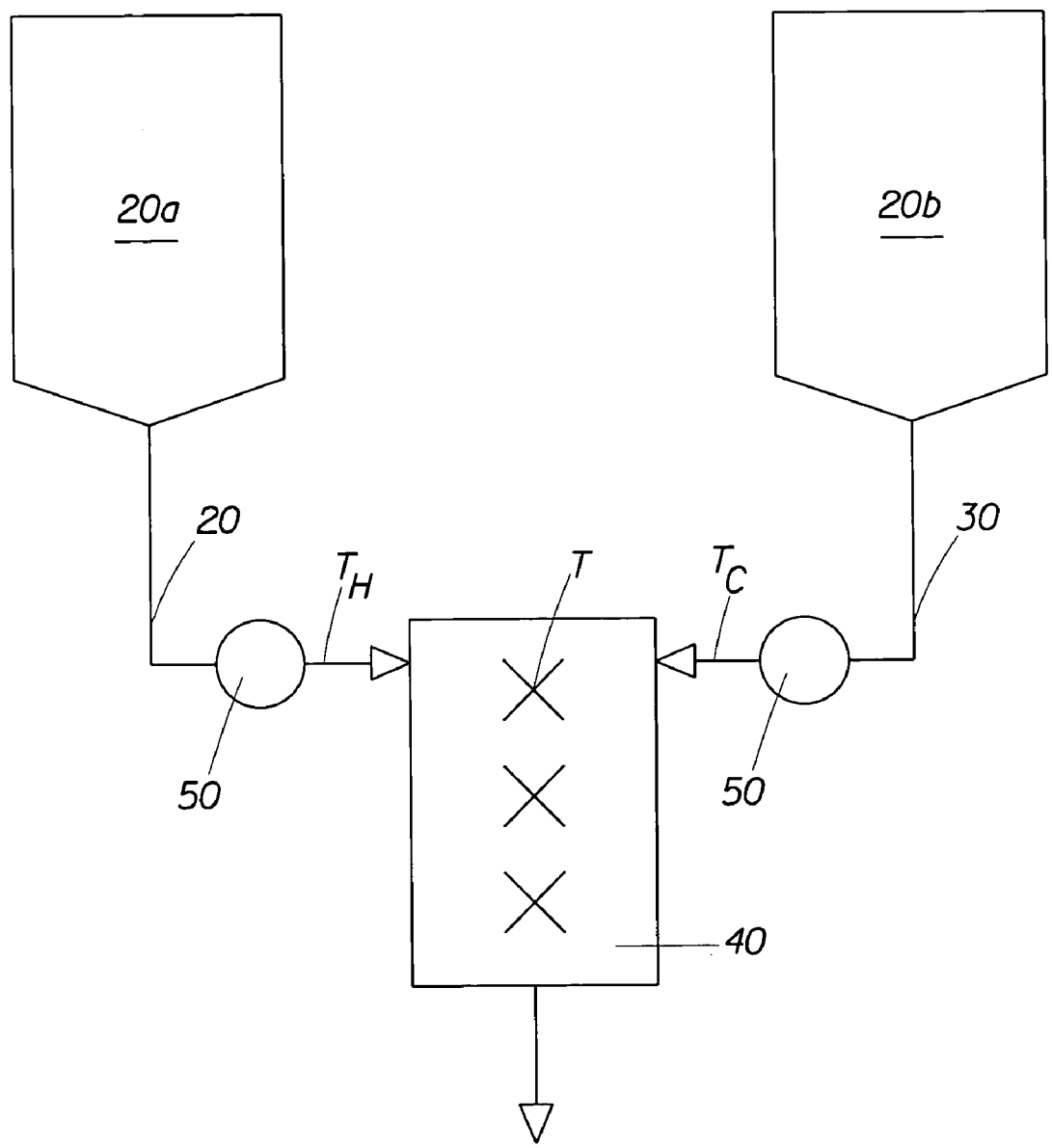
FIG. 1 is a schematic diagram of the direct contact quench-crystallization process of the present invention.

The term "anhydrous" as used herein with respect to the product of the present invention means that the antiperspirant stick composition of the present invention, and the essential or optional components thereof are substantially free of added or free water. From a formulation standpoint, this means that the anhydrous antiperspirant stick compositions of the present invention contain less than about 5%, more specifically less than about 3%, even more specifically less than about 1%, and even more specifically zero percent, by weight of free or added water, other than the water of hydration typically associated with the particulate antiperspirant active prior to formulation.

The term "onset of crystallization" as used herein, means the temperature at which a material crystallizes from a liquid solution. All melt points and the onset of crystallization referenced herein, unless otherwise specified, are measured by the well known technique of Differential Scanning Calorimetry (DSC). For evaluation a Perkin-Elmer 7 Series Thermal Analysis System Model DSC7 is used, manufactured by Perkin-Elmer, Norwalk, Conn.

The term "ambient conditions" as used herein refers to surrounding conditions comprising about one atmosphere of pressure, at about 50% relative humidity, and at about 25° C. All values, amounts and measurements described herein are obtained under ambient conditions unless otherwise specified.

The term "volatile" as used herein refers to those materials which have a measurable vapor pressure at 25° C. Such vapor pressures will typically range from about 0.01 millimeters Mercury (mmHg) to about 6 mmHg, more typically from about 0.02 mmHg to about 1.5 mmHg, and have an average boiling point at one atmosphere (atm) of pressure of less than about 250° C., more typically less than about 235° C. at one atm. Conversely, the term "non-volatile" refers to those materials which are not "volatile" as defined herein.

The term "direct quench" crystallization, as used herein, refers to a cooling process resulting from instantaneously combining together a hot process stream containing a liquid gellant, and a cold process stream, thereby causing substantially the entire amount of the gellant contained in the hot stream being mixed to instantaneously cool to a temperature below the onset of crystallization of the gellant. The term "direct" in this context means that the cold and hot process streams contact one another, and heat and mass transfer occurs, without any layer or other separation between the streams.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

In essence, the process of the present invention can be accomplished by combining at least two process streams, at least one hot process stream 20 and at least one process stream 30, within a mixing chamber 40, FIG. 1. In FIG. 40, a tank containing a hot process stream components is designated as 20a; and a tank containing a cold process stream components is designated as 20b. Conventional equipment, such as, for example, pumps 50 can be used to facilitate movement of the hot and cold streams 20, 30 towards and into the mixing chamber 40.

The mixing chamber 40 may comprise a pipe, a any other suitable arrangement capable of receiving both the hot process stream 20 and the cold process stream 30 therein so that the streams 20 and 30 are combined therein with sufficient turbulence to cause thorough mixing and heat transfer. The mixing chamber 40 may be a small void space containing static baffles or other physical structure arranged to enable thorough mixing and heat transfer between the hot and cold process streams 20, 30.

A hot process stream 20 may contain a gellant melted in a solvent base and held above the full melting point of the gellant. A cold process stream 30 may contain solvent, antiperspirant active, and any heat-sensitive components.

Beneficially, the ratio of the hot process stream to the cold process stream at the point of combining the streams together may be from about 1:9 to about 3:1, i.e., the hot process stream may comprise be from about 10 percent to about 75 percent of the cold process stream.

Given a certain proportion of the hot and cold process streams within the required range, the cold process stream must have a temperature sufficient to cause substantially the entire amount of the hot process stream being mixed to cool to a temperature that is at least one degree C. lower than the onset of crystallization of the gellant, when the hot and cold process streams are combined within the mixing chamber 40. More specifically, the temperature of the product stream within the mixing chamber 40 is at least 5° C., more specifically at least 10 degrees, C. lower that the onset of crystallization of the gellant. The cool process stream can be held at ambient temperature. The at least two process streams 20, 30 are then instantaneously combined and mixed within a mixing chamber 40 to effect a quench cooling rate of the "hot" stream of at least 30° C. per second, more specifically at least 50° C. per second, and more specifically at least 100° C. per second.

One skilled in the art will appreciate that if the process of the present invention is run continuously, the relative proportions of the hot and cold process streams should be computed taking into consideration the hot and cold streams' respective heat and mass flow properties to achieve the desired quench.

The term "at least one" process stream is intended to convey that the present invention is not limited to mixing just two streams; one skilled in the art will understand that each of the hot and cold process streams may comprise several hot or cold streams. Put another way, the present invention contemplates mixing multiple hot process streams 20 and multiple cold process streams 30.

The temperature of the hot process stream, the cold process stream, and the resulting, combined, product stream can be measured by any method known in the art. The temperature of the hot process stream Th and the temperature of the cold process stream Tc can be measured just before the two streams combine; and the temperature of the product stream T can be measured right after the hot and cold streams have been combined, as schematically shown in FIG. 1.

Hot Process Stream

The step of forming a hot process stream involves mixing a solvent and a gellant so that the gellant is dissolved in the solvent. The hot process stream has a first temperature that may range from 1° C. to 50° C. above the onset of crystallization of the hot process stream. The gellant and solvent may be combined and mixed using a static mixer or alternately may be combined and mixed in a hot process tank 20a using conventional process equipment obvious to those skilled in the art.

The solvent can be any material that is liquid at the holding temperature of the hot process stream and that can essentially completely dissolve the gellant. The solvent can be selected from the group consisting of cyclic, linear and branched chain silicones. Suitable solvents may comprise, but are not limited to, non-volatile paraffinic hydrocarbon fluids such as those described in U.S. Pat. No. 4,985,238 and anhydrous liquid carriers such as those described in U.S. Pat. No. 6,171,601 or in U.S. Pat. No. 6,258,346 and emollients such as those described in U.S. Pat. No. 5,972,319. Solvent comprising cyclomethicone is believed to be beneficial.

The gellant can be any material which can crystallize from the hot process stream and remain solid at room temperature. Suitable gellants can include, but are not limited to, those described in U.S. Pat. No. 6,258,346 and those described as nucleating agents or gellants in U.S. Pat. No. 6,171,601, or those waxes and wax-like materials described in U.S. Pat. No. 4,985,238 and may be selected from, but not limited to, the group consisting of stearyl alcohol and other fatty alcohols; hydrogenated castor oil; paraffin wax; beeswax; carnauba; candelilla; spermeceti wax; ozokerite; ceresin; baysberry; synthetic waxes, such as Fisher-Tropsch waxes and microcrystalline wax; polyethylenes with molecular weight of about 200 to about 1000 daltons; solid triglycerides; and any mixtures thereof.

Cold Process Stream

The step of forming a cold process stream involves mixing an antiperspirant or deodorant or cosmetic active, as described herein, and a solvent and optionally a heat sensitive component. The cold stream has a second temperature that is at least 10 degrees C. below the onset of crystallization of the gellant in the hot stream. The second temperature is at least about 20 degrees lower than the first temperature. More specifically, the second temperature is at least 50 degrees, and even more specifically at least 70 degrees C. lower than the first temperature.

The cold process stream may include a liquid emollient or solvent. Suitable liquid emollients or solvents may be selected from the group consisting of mineral oil; PPG-14 butyl ether; isopropyl myristate; petrolatum; butyl stearate; cetyl octanoate; butyl myristate; myristyl myristate; C12-15 alkylbenzoate (e.g., Finsolv.TM.); octyldodecanol; isostearyl isostearate; octododecyl benzoate; isostearyl lactate; isostearyl palmitate; isobutyl stearate; dimethicone and any mixtures thereof.

The cold process stream comprises a liquid emollient or solvent that is characterized by its ability to disperse an antiperspirant or deodorant active or a cosmetic active. The liquid emollient for the cold process stream may comprise, but is not limited to, the aforementioned solvents for use in the hot process stream. The liquid emollient or solvent can be selected from the group consisting of cyclomethicone, mineral oil; PPG-14 butyl ether; isopropyl myristate; petrolatum; butyl stearate; cetyl octanoate; butyl myristate; myristyl myristate; C12-15 alkylbenzoate (e.g., Finsolv.TM.); octyldodecanol; isostearyl isostearate; octododecyl benzoate; isostearyl lactate; isostearyl palmitate; isobutyl stearate; dimethicone and any mixtures thereof.

The cold process stream may also optionally comprise any heat sensitive component that could chemically degrade or deteriorate or react with components of the cosmetic or antiperspirant composition at elevated temperatures or corrode metal process equipment at elevated storage temperatures. Suitable antiperspirant actives and suitable cosmetic actives may include, but are not limited to those described below. Preferably the cold process stream contains the antiperspirant active.

Combining Hot and Cold Process Streams

The step of combining the at least one hot process stream and the at least one cold process stream together involves combining the streams in such a manner as to cause substantially complete mixing and heat transfer between the hot process stream and the cold process stream in a very short time period. The time period during which such mixing and heat transfer occur according to the present invention is less than 3 seconds, more specifically less than 1 second. This causes the gellant to cool at a cooling rate of at least 30 degrees C. per second, thereby crystallizing the gellant and forming the solid cosmetic composition. The gellant component can be cooled to a temperature of from 35° C. to 55° C., the temperature at which the gellant component crystallizes.

During the step of combining the at least one hot process stream and the at least one cold process stream together, substantially the entire amount of the hot process stream is cooled to the temperature of at least 1 degree, more specifically at least 5 degrees, and even more specifically at least 10 degree C., below the onset of crystallization of the product stream.

One of the advantages of this invention is that combining the hot and cold process streams together in a manner as to effect direct contact quench cooling having no external sources of cooling allows for greater nucleation which produces very small crystals—less than about 10 microns—in the resulting product.

The the step of combining the hot process stream and the cold process stream may be conducted a pipe having an external source of heating involving no moving mechanical parts. Such an arrangement eliminated the disadvantages of the known in the art conventional-type processes requiring relatively expensive equipment and its necessary maintenance.

In another aspect, the present invention comprises a solid cosmetic composition made by the process of the present invention and comprising an antiperspirant or deodorant active, wherein the cosmetic composition has an average crystal size of less than about 10 microns. As one skilled in the art will recognize, the crystal size can be measured by using cross-polarized light microscopy methods. As used herein, the "average" crystal size refers to a mean size of the major (largest) axis of a crystal, averaged across at least 20 measurements in at least three separate samples made according to the process of the present invention. Put another way, to measure the average crystal size, one would need to prepare at least three separate samples of the product as described herein, and then measure at least twenty random and representative crystals in each of the samples. The results are then arithmetically averaged.

Antiperspirant Active

The antiperspirant and deodorant embodiments of the present invention may comprise an aluminum-containing antiperspirant active suitable for application to human skin. The concentration of the active should be sufficient to provide the desired perspiration wetness or odor control from the formulation selected.

The antiperspirant active concentration in the antiperspirant and deodorant embodiments of the present invention ranges from about 0.1% to about 30%, more specifically from about 5% to about 30%, by weight of the composition. These weight percentages are calculated on an anhydrous metal salt basis exclusive of water and any complexing agents such as glycine, glycine salts, or other complexing agents. The antiperspirant active can be solubilized or solid, but is preferably in the form of a dispersed solid particulate. The dispersed particulates most typically have average particle size or diameter of less than about 100 micron, more typically from about 1 micron to about 40 micron. The particle size can be measured by using light microscopy methods or any light-scattering technique known in the art.

The antiperspirant active for use in the antiperspirant and deodorant embodiments of the present invention include any aluminum-containing material having antiperspirant activity, which can be used alone or in combination with other antiperspirant active materials such as zirconium-containing actives. The antiperspirant actives suitable for use herein include astringent metallic salts, especially inorganic and organic salts of aluminum, zirconium and zinc, as well as mixtures thereof. Particularly beneficial are aluminum—containing and/or aluminum/zirconium—containing salts or materials, such as aluminum halides, aluminum chlorohydrate, aluminum hydroxyhalides, zirconyl oxyhalides, zirconyl hydroxyhalides, and mixtures thereof.

Beneficial are aluminum salts for use in the antiperspirant and deodorant embodiments of the present invention include those that conform to the formula:

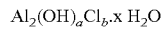

$$Al_2(OH)_aCl_b \cdot x\, H_2O$$

wherein a is from about 2 to about 5; the sum of a and b is about 6; x is from about 1 to about 6; and wherein a, b, and x may have non-integer values. Aluminum chlorohydroxides referred to as "5/6 basic chlorohydroxide", wherein a=5, and "2/3 basic chlorohydroxide", wherein a=4, are believed to be beneficial. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Beneficial zirconium salts for use in the antiperspirant and deodorant embodiments of the present invention include those which conform to the formula:

$$ZrO(OH)_{2-a}Cl_a \cdot x\, H_2O$$

wherein a is from about 1.5 to about 1.87; x is from about 1 to about 7; and wherein a and x may both have non-integer values. These zirconium salts are described in Belgian Patent 825,146, Schmitz, issued Aug. 4, 1975, which description is incorporated herein by reference. Particularly beneficial zirconium salts are those complexes which additionally contain aluminum and glycine, commonly known as ZAG complexes. These ZAG complexes contain aluminum chlorohydroxide and zirconyl hydroxy chloride conforming to the above-described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, all of which are incorporated herein by reference.

Antiperspirant actives suitable for use in the compositions include aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum zirconium trichlorohydrate, aluminum zirconium tetrachlorohydrate, aluminum zirconium pentatchlorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, aluminum chloride, aluminum sulfate buffered, and combinations thereof. Further suitable antiperspirant actives are described in U.S. Pat. No. 6,663,854 or in U.S. 20040009133, the descriptions of which are incorporated herein by reference.

Deodorant Active

The antiperspirant and deodorant compositions of the present invention can also be formulated with an underarm active in the form of an antimicrobial deodorant material in addition to or in place of the antiperspirant active. Deodorant active concentrations in the compositions can range from about 0.1% to about 30%, specifically from about 0.1% to about 10%, even more specifically from about 0.1% to about 3%, by weight of the composition. These deodorant actives include any known or otherwise safe and effective antimicrobial deodorant active suitable for topical application to human skin, and which is effective in preventing or eliminating malodor associated with perspiration.

Non-limiting examples of antimicrobial deodorant actives for use in the antiperspirant and deodorant compositions of the present invention include cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichlorio-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof. Triclosan, triclocarban, and combinations thereof are believed to be beneficial.

Other deodorant actives suitable for use herein are described in U.S. Pat. No. 6,013,248 (Luebbe et al.), which descriptions are incorporated herein by reference.

Cosmetic Actives

The cosmetic stick compositions of the present invention comprise from about 0.01% to about 60% by weight of a cosmetic active. Suitable actives include any known or otherwise effective cosmetic active that is compatible with the essential ingredients of the cosmetic sticks of the present invention, or which do not otherwise unduly impair the product performance thereof.

Cosmetic actives suitable for use in the compositions of the present invention include moisturizers, emollients, perfumes or fragrances, skin conditioners, antiperspirants, anti-oxidants, vitamins, anti-wrinkle products, surfactants, pharmaceuticals, deodorants, pigments or colorants, sunscreens or other photo protectants, and any other material intended or otherwise suitable for topical application to the skin.

Non-limiting examples of cosmetic actives suitable for use herein are described in U.S. Pat. No. 6,001,377 (SaNogueira, Jr. et al.), U.S. Pat. No. 6,024,942 (Tanner et al.), U.S. Pat. No. 6,013,271 (Doughty et al.), and U.S. Pat. No. 6,013,270 (Hargraves et al.), U.S. Pat. No. 6,013,248 (Luebbe et al.) U.S. Pat. No. 5,976,514 (Guskey et al.), which descriptions are hereby incorporated herein by reference.

Specific examples of cosmetic actives suitable for use herein include antiperspirant and deodorant actives as described herein, perfumes and fragrances, antimicrobials (antibacterial, antifungal), steroidal anti-inflammatory materials (e.g., hydrocortisone), non-steroidal anti-inflammatory materials, vitamins and derivatives thereof (e.g., thiamin, riboflavin, niacin, pyridoxine, vitamin A, vitamin D, vitamin E, vitamin K), hydroxy and alpha-hydroxy acids (e.g., salicylic acid, citric acid), moisturizers (e.g., silicone and non-silicone), and the like.

Non-limiting embodiments of the cosmetic stick compositions of the present invention include lipsticks, foundations and makeup, antiperspirant and deodorant sticks, suncreen or other photoprotective sticks, emollient sticks, health care actives delivered from a solid stick (e.g., steroidal and non-steroidal anti-inflammatory agents, analgesic stick, etc.), or any other solid stick embodiment from which a desired material, skin active or inert, is incorporated into for topical delivery to the skin.

Differential Scanning Calorimetry Method For Evaluating Complete Melt Point 1. 10 mg of sample is weighed into a three-component volatile sample pan arrangement, comprising a bottom, a lid, and rubber seal. The assembled sealed pan resists loss of volatile components and is beneficial to accurately measure the melt points described herein.

2. The pan is then heated from 0° C. to 150° C. at a rate of 5° C./minute.

3. The complete melt point is determined as the temperature at the intersection of the baseline tangent to the trailing edge of the endothermic peak.

Method for Determining Onset Of Crystallization 1. 10 mg of sample is weighed into a three-component volatile sample pan arrangement, comprising a bottom, a lid, and rubber seal. The assembled sealed pan resists loss of volatile components and is beneficial to accurately measure the melt points described herein.
2 The pan is then cooled from 100° C. to 0° C. at a rate of 5° C./minute.
3. The onset of crystallization is determined as the temperature at the intersection of the baseline tangent to the leading edge of the exothermic peak.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. A method of solidifying a cosmetic composition comprising an antiperspirant or deodorant active, the method comprising the steps of:
    (a) providing a liquid gellant component in a first liquid solvent having a first temperature;
    (b) providing an active component dispersed in a second liquid solvent having a second temperature lower than the first temperature;
    (c) combining the liquid gellant component and the active component together so that the active component causes instantaneous cooling of the gellant component to a temperature of from 35° C. to 55° C., thereby crystallizing the gellant component, with the proviso that the cooling of the gellant is conducted with no external sources of cooling.

2. The method of claim 1, wherein the gellant is selected from the group consisting of stearyl alcohol and other fatty alcohols; hydrogenated castor oil; paraffin wax; beeswax; carnauba; candelilla; spermeccti wax; ozokerite; ceresin; baysberry; synthetic waxes, such as Eisher-Tropsch waxes and microcrystalline wax; polyethylencs with molecular weight of about 200 to about 1000 daltons; solid triglycerides and any mixtures thereof.

3. The method of claim 1, wherein the first temperature is from about 1° C. to about 50° C. above the onset of crystallization of the gellant.

4. The method of claim 1, wherein the second temperature is at least 20° C. below the first temperature.

5. The method of claim 1, wherein the second temperature is at least 50° C. below the first temperature.

6. The method of claim 1, wherein the second temperature is at least 70° C. below the first temperature.

7. The method of claim 1, wherein the instantaneous cooling comprises cooling the gellant and first liquid solvent at a rate of at least 30° C. per second via combining step (c).

8. The method of claim 1, wherein the instantaneous cooling comprises cooling the gellant and first liquid solvent at a rate of at least 50° C. per second via combining step (c).

9. The method of claim 1, wherein the instantaneous cooling comprises cooling the gellant and first liquid solvent at a rate of at least 100° C. per second via combining step (c).

10. The method of claim 1, wherein the method is a continuous process.

11. The method of claim 10, wherein each of the providing steps (a) and (b) comprises a supply tank and a stream flowing therefrom.

12. The method of claim 11, wherein in step (c) the individual streams are brought together in a mixing chamber.

13. The method of claim 12, wherein the mixing chamber comprises a static mixer.

* * * * *